United States Patent [19]
Kalidindi

[11] Patent Number: 5,726,363
[45] Date of Patent: Mar. 10, 1998

[54] LIQUID SAMPLER

[76] Inventor: Sanyasi R. Kalidindi, 15 Edinburg La., East Brunswick, N.J. 08816-5242

[21] Appl. No.: 552,052

[22] Filed: Nov. 2, 1995

[51] Int. Cl.[6] .............................. G01N 1/14; B01C 3/02
[52] U.S. Cl. ...................... 73/864.14; 73/864.13; 73/864.18
[58] Field of Search ................... 73/864.14, 864.16, 73/864.18, 864.13

[56] References Cited

U.S. PATENT DOCUMENTS

| | | | |
|---|---|---|---|
| 1,946,651 | 2/1934 | Viruette | 141/110 |
| 2,189,238 | 2/1940 | Benjamin | 73/864.63 |
| 2,792,834 | 5/1957 | Kapelsohn | 73/864.16 X |
| 2,916,057 | 12/1959 | Carle et al. | 73/864.16 |
| 2,959,964 | 11/1960 | Streitfeld | 73/864.14 |
| 3,242,740 | 3/1966 | Niskin | 73/863.31 |
| 3,675,492 | 7/1972 | Tejera | 73/864.18 |
| 3,692,490 | 9/1972 | Hall | 422/99 |
| 3,754,863 | 8/1973 | Reunanen | 73/864.16 X |
| 3,766,785 | 10/1973 | Smernoff | 73/864.14 |
| 3,826,144 | 7/1974 | Wessels | 73/863.31 |
| 4,016,765 | 4/1977 | Lee | 73/864.15 |
| 4,172,385 | 10/1979 | Cristensen | |
| 4,567,780 | 2/1986 | Oppenlander et al. | 73/864.16 |
| 4,679,446 | 7/1987 | Sheehan et al. | 73/864.14 X |
| 4,734,261 | 3/1988 | Koizumi et al. | 422/100 |
| 4,744,955 | 5/1988 | Shapiro | 73/864.14 X |
| 4,933,148 | 6/1990 | Perlman | 73/864.14 X |
| 5,104,624 | 4/1992 | Labriola | 422/100 |
| 5,192,511 | 3/1993 | Roach | 73/864.14 X |
| 5,343,909 | 9/1994 | Goodman | 141/242 |
| 5,380,486 | 1/1995 | Anami | 422/63 |
| 5,431,067 | 7/1995 | Anderson et al. | 73/863.86 |
| 5,456,879 | 10/1995 | Suovaniemi | 73/864.14 X |

FOREIGN PATENT DOCUMENTS

| | | | |
|---|---|---|---|
| 858148 | 12/1952 | Germany | 73/864.16 |
| 2021971 | 12/1979 | United Kingdom | 73/864.16 |
| 2032885 | 5/1980 | United Kingdom . | |

*Primary Examiner*—Thomas P. Noland
*Attorney, Agent, or Firm*—Richard C. Litman

[57] ABSTRACT

A sampling device having sampling receptacles with specific volumes are attached on the liquid sampler's receiving area for the purpose of taking unit dose samples of a liquid. The liquid sampler includes a receptacle with a central opening in the receptacle's bottom which is attached to an elongated tube. An elongated rod moves axially within the tube and a coupling nut engages the receptacle, thus firmly gripping the tube. The liquid sampler draws liquid samples into the sampling receptacle so that content uniformity testing may be carried out to assure uniform distribution of active ingredients throughout a product batch before the product is sent to market.

5 Claims, 5 Drawing Sheets

LIQUID SAMPLER

BACKGROUND OF THE INVENTION

1. Field of the Invention

The present invention relates generally to sampling and measuring. More specifically, the invention relates to a liquid sampling device for taking precise samples from a body of a pharmaceutical liquid. Even more specifically, the invention relates to a sampling device wherein sampling receptacles having specific volumes can be attached on the liquid sampler's receiving area. The sampling can be done at a single location or multiple locations in a mixer or a tank for the purpose of taking unit dose samples of the pharmaceutical liquid.

2. Description of the Prior Art

The formulation of pharmaceutical, food or cosmetic liquid products or any other heterogeneous systems involves the dispersion or dissolution of the active ingredient(s) or drug(s) in the inert ingredients such as water, sugar syrup and the like, and stabilized with other inert ingredients, such as suspending agents, sweeteners and flavors. The product has to be tested for uniform distribution of the active ingredient(s) throughout the product batch before the product is sent to market. This type of testing is known in the industry as content uniformity testing. In order to perform content uniformity testing properly, samples are taken from various locations in the batch, analyzed for active content, and the coefficient of variation is calculated.

The coefficient of variation must be within certain limits for the product to pass the test. The results of such testing depend on, among other factors, the sample size and sampling procedure. A unit dose is equal to one dose of the product. In order for the content uniformity test to be meaningful, the sample size should be as close to the unit dose as possible and the sampling procedure should cause minimal disturbance in the product.

The usual practice of performing the content uniformity test requires taking samples while the liquid is being discharged from the mixer or tank. A disadvantage to this procedure of sampling is that it is very hard to get unit dose samples. In addition, this procedure complicates determining from which points in the mixer or the tank the samples are obtained. Also, the samples are usually obtained from a running stream which does not represent true homogeneity of the product.

The present invention overcomes these drawbacks by providing: (1) a sampling device configured to take samples from a body of pharmaceutical solution that is not moving and is more representative of the final product and therefore, more accurate; (2) a sampling device capable of determining from which locations in the mixer or tank the samples have been taken; (3) a sampling device where a variety of sampling receptacles, each one having a precise volume, are interchangeable with the device; (4) a sampling device where sampling receptacles of various sizes may be used simply by changing the adapter; (5) a sampling device utilizing sterile disposable sampling receptacles.

A number of patents have been issued for liquid samplers. In U.S. Pat. No. 5,431,067 issued on Jul. 11, 1995 to John D. Anderson et al. there is disclosed a sampler mechanism by which a liquid sample can be drawn into a closed container without exposing the sample to the atmosphere or the operator taking the sample.

In U.S. Pat. No. 1,946,651 issued on Feb. 13, 1934 to Joseph D. Viruette there is disclosed a device for removing a measured quantity of liquid from a bottle.

In U.S. Pat. No. 2,189,238 issued on Feb. 6, 1938 to Israel J. Benjamin there is disclosed a sampling dipper where a vertical rod manually actuates a valve which permits the sampling and dispensing of a liquid sample.

In U.S. Pat. No. 4,172,385 issued on Oct. 30, 1979 to Melford K. Cristensen there is disclosed a sampling device insertable lengthwise through a tank opening to take a vertical, cross sectional sampling of tank contents. The sampling device includes a transparent tube of cross section to freely admit tank contents as the tube is lowered into contact with the tank bottom wall.

In U.S. Pat. No. 3,242,740 issued on Mar. 29, 1966 to Shale J. Niskin there is disclosed a sampling device for obtaining multiple samples substantially simultaneously at various depths.

In U.S. Pat. No. 3,766,785 issued on Oct. 23, 1973 to Ronald B. Smernoff there is disclosed a positive action pipette for drawing and discharging defined quantities of liquid. The pipette has a disposable tip portion that may be ejected after liquid has been discharged.

In U.S. Pat. No. 4,016,765 issued on Apr. 12, 1977 to Tsao-Piao Lee there is disclosed a pipette controller with a graduate reading device for presetting the volume of liquid to be drawn.

None of the above inventions and patents, taken either singly or in combination, is seen to describe the instant invention as claimed.

SUMMARY OF THE INVENTION

The present invention is a liquid sampler for taking unit dose samples of a pharmaceutical liquid from a single location or multiple locations in a mixer or a tank. The sampler gives the advantage of using a bottle or sterile disposable syringes to collect the samples. Different bottle and syringe sizes may be used by changing the adapter of the sampler. The sampler with the syringe has a scale etched on the top of the sampler to exactly match the scale on the syringe, thus assuring accurate sample volumes. Embodiments of the present invention are provided that are specifically designed for portability, for disposability, for use with a bottle, a syringe, multiple syringes, and for easy, temporary use.

Accordingly, it is a principal object of the invention to take unit dose samples of a pharmaceutical liquid from a single location or multiple locations in a mixer or a tank.

It is another object of the invention to use a bottle or a sterile disposable syringe as sampling receptacles.

It is a further object of the present invention to take samples from a body of pharmaceutical liquid that accurately reflect the liquid's composition.

It is another object of the present invention to be able to determine the location in the mixer or tank that the sample was taken.

It is a further object of the present invention to use a sampling device that has a variety of sampling devices, each with a precise volume, that are interchangeable with the sampler.

It is another object of the present invention to accurately draw and deliver quantities of samples that do not require exercising human judgment in evaluating the quantity being drawn.

It is also an object of the present invention to provide a sampler which accurately draws and delivers liquid samples in small quantities.

It is further an object of the present invention to provide a sampler that is suitable for repetitive usage and does not become contaminated.

It is a further object of the present invention to design a sampler having a minimum number of critical sealing surfaces that minimize the possibility of leaks.

It is also an object of the present invention to provide a graduated scale in the volume adjustment assembly that is convenient to use and easy to read and which does not interfere with the use of the device.

It is also an object of the present invention to use a sampling device where sampling receptacles of various sizes may be used by changing the adapter.

It is a further object of the present invention to use sterile disposable sampling receptacles.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
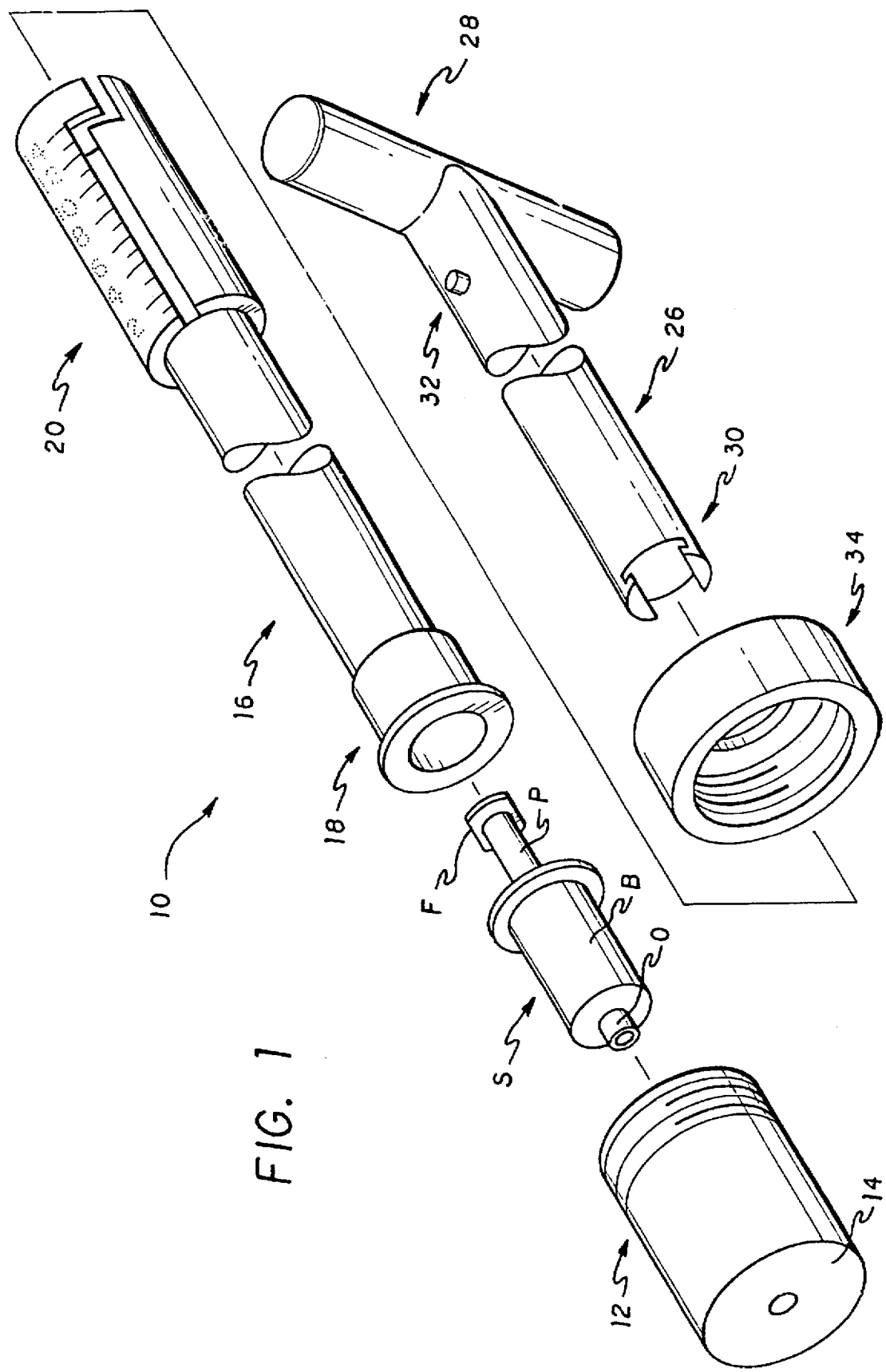
FIG. 1 is an exploded view of the preferred embodiment of the present invention.
Figure 2:
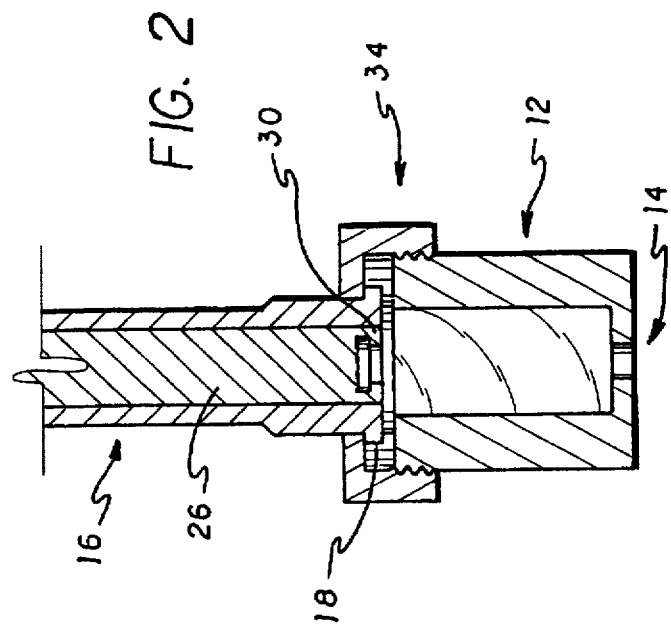
FIG. 2 is a cross-sectional view of the sampling device of FIG. 1.

Referring to FIGS. 1 and 2, the preferred embodiment of the liquid sampler 10 is shown. The liquid sampler 10 has a receptacle 12 with a central opening 14 in the bottom 12 of the receptacle. An elongated tube 16 abuttingly communicates with the receptacle 12. An elongated rod 26 moves axially within the tube 16 and a coupling nut 34 that threadably engages the receptacle 12, thus firmly gripping the tube 16.

Referring now to FIG. 1, it can be seen that the receptacle 12 is dimensioned to hold a standard syringe S having an inlet opening O. The receptacle 12 has a cylindrical sidewall. The central opening 14 of the receptacle 12 allows the inlet opening O of the syringe S to communicate with the space outside of the receptacle 12 and to draw a sample of the liquid into the syringe. The internal cavity of the receptacle 12 is dimensioned to house the barrel portion B of the syringe.

An elongated tube 16 is configured to abuttingly communicate with the top opening of the receptacle 12. The tube has a bore and first and second ends. The second end of the tube 16 has a flange 18 that is dimensioned and configured to abuttingly contact the top opening of the receptacle 12. A coupling nut 34 having a central opening with a diameter that is smaller than the tube 16 joins the tube 16 and the receptacle 12. The coupling nut 34 is threadably engageable with the receptacle 12 such that the flange 18 is firmly gripped between the coupling nut 34 and the receptacle 12.

An elongated rod 26 having a first end and a second end is dimensioned and configured to move axially within the bore of the tube 16. The first end of the rod 26 has a cylindrical bar attached at a right angle to the first end of the rod 26 such that a T-shaped handle 28 is formed. The second end of the rod 26 has a T-shaped groove 30 that is dimensioned and configured to grip the pressure platform F of a plunger P. The T-shaped groove 30 allows the rod 26 to releasably attach the plunger.

Figure 3:
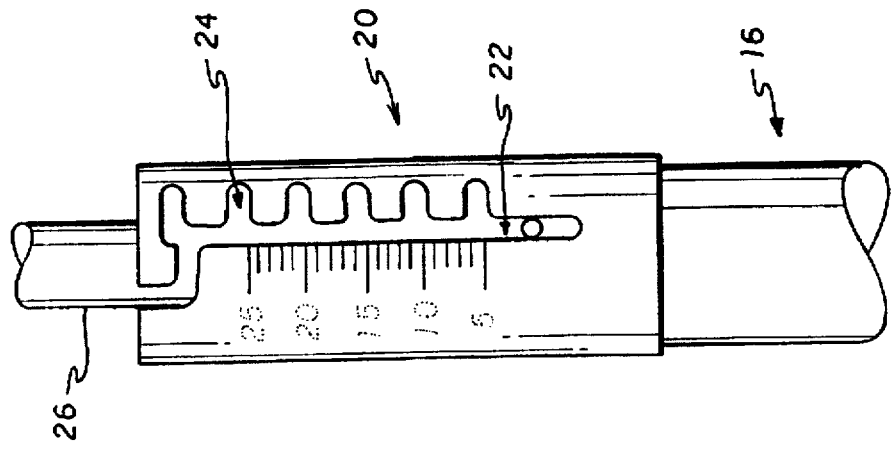
FIG. 3 is an elevational view of the graduated scale of the present invention.

The rod 26 has a protuberance 32 located near the first end. The tube 16 has a volume scale sleeve 20 near the first end. Turning to FIG. 3 for more specific details of the volume scale sleeve 20, there is a guiding slot 22 in the volume scale sleeve 20 for receiving the protuberance 32. The volume scale sleeve 20 has indicia that are next to the guiding slot 22 that allow the user to determine the volume of the liquid sample in the syringe by inspection. If the user desires a specific volume be drawn, the volume scale sleeve 20 also has a plurality of locking slots 24 corresponding in their positions to a respective value for the volume of the sample of the liquid in the syringe. The locking slots 24 allow the user to lock the protuberance 32 in a specific locking slot 24 and fix the volume of the liquid sample to be drawn into the syringe.

In use, the receptacle 12 is placed in the body of liquid from which the liquid sample is to be taken. By manipulating the elongated rod 26 axially within the tube 16, the T-shaped groove 30 of the rod 26 moves the plunger of the syringe in an axial direction within the tube 16. The axial movement of the plunger creates a pressure within the barrel of the syringe. The pressure thereby draws a sample of the liquid through the inlet opening of the syringe. Since the indicia on the volume scale sleeve 20 corresponds to the volume indicia on the syringe, the user can determine the volume of the liquid sample drawn by inspecting the location of the protuberance 32 relative to the volume scale sleeve 20. The liquid sampler 10 provides the advantage of using sterile disposable syringes to collect the liquid samples, which will assure the validity of the sample drawn. Also, the liquid sampler 10 provides the taking of unit dose samples, as small as 0.1 cc, from a user determined location It should also be noted that, although in the embodiment discussed here only one tube 16 and one rod 26 is discussed, any number of these can be arranged in an end-to-end arrangement with one another, leading to a liquid sampler of user determined length. All that is required is to have a tube 16 with a corresponding length. It should also be noted that although a T-shaped handle 30 is shown as the manipulating member, any number of appropriate shapes such as a ring or other shape could be used in the T-shaped handles 30 place to facilitate the manipulation of the device.

Figure 4:
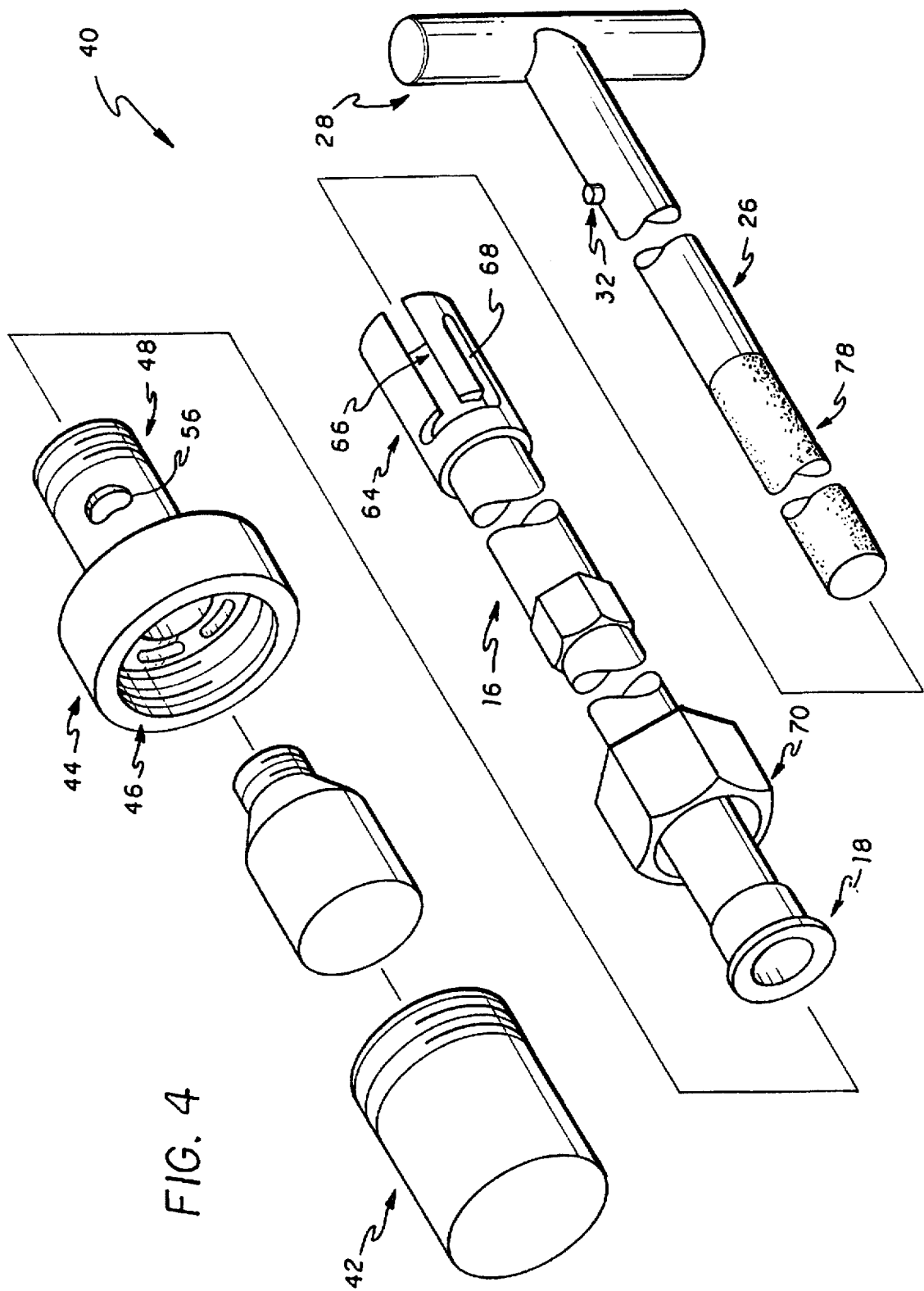
FIG. 4 is an exploded view of an alternative embodiment of the present invention.
Figure 5:
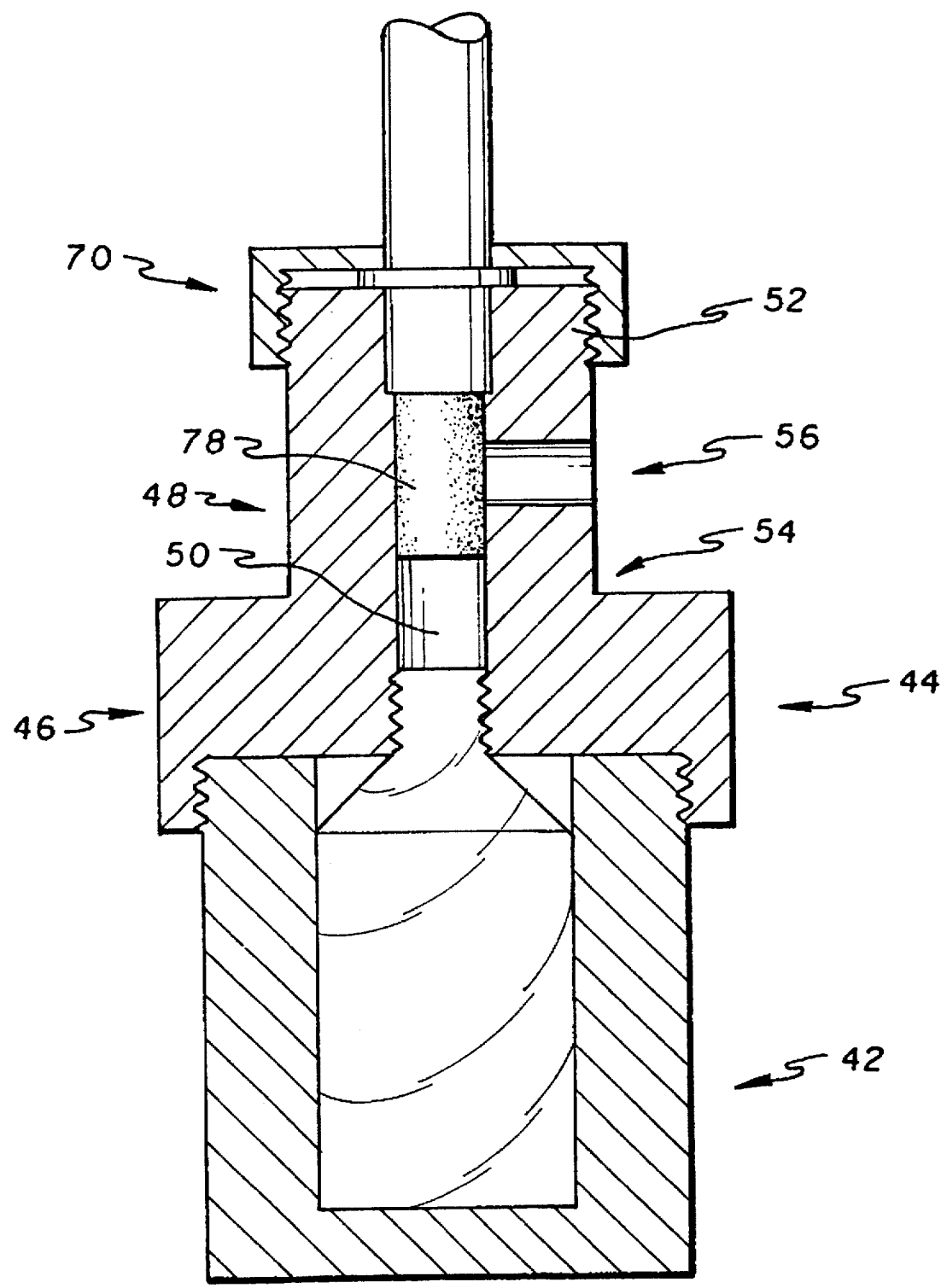
FIG. 5 is a cross-sectional view of FIG. 4.
Figure 6:
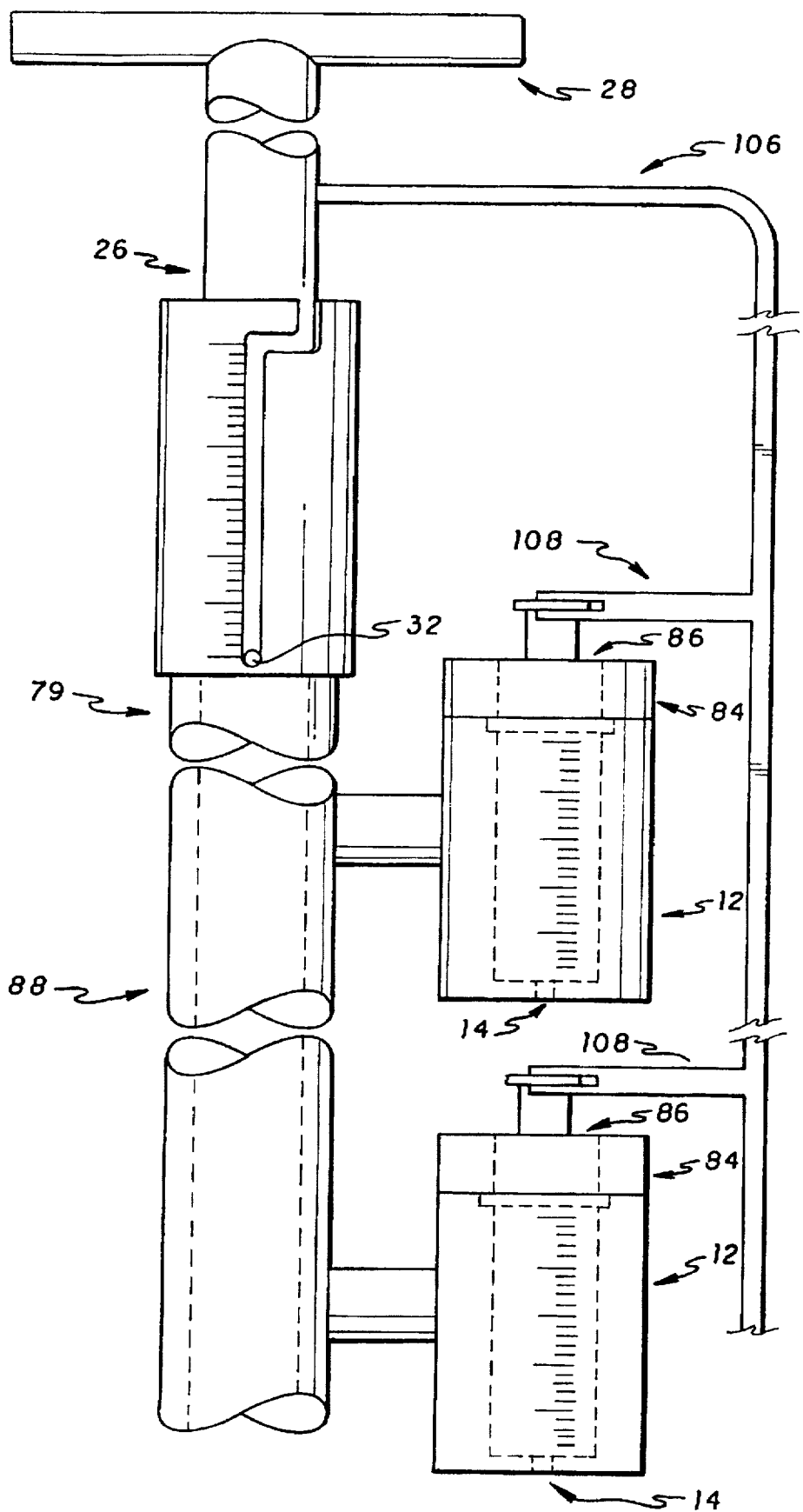
FIG. 6 is a perspective view of a third embodiment of the present invention.

Turning to FIGS. 4 and 5, an alternative liquid sampler 40 is shown. In this embodiment, a sampling bottle is used to store the drawn liquid sample. The alternative liquid sampler 40 has a receptacle 42 having a top opening and an internal cavity that is dimensioned and configured to house the sample bottle. A coupling adapter 44 is threadably engaged to the receptacle 42 such that the coupling adapter 44 acts as a closure for the receptacle 42. An elongated tube 16 abuttingly contacts the coupling adapter 44. An elongated rod 26 with a polytetrafluoroethylene (PTFE) coated sealing plug 78 on the end 26 of the rod that moves axially within the tube 16.

Referring to FIGS. 4 and 5, it can be seen that the receptacle 42 is dimensioned to hold a standard sampling bottle having a threaded mouth that is in open communication with an internal storage space. The coupling adapter 44 has first diameter and second diameter portions 46, 48. The first diameter portion 46 is threadably engageable with the top opening of the receptacle 42 whereby the coupling adapter 44 acts as a closure for the receptacle 42. The second diameter portion 48 of the coupling adapter 42 is attached to the first diameter portion 46 and has a central passage 50 that extends between the second diameter portions' 48 first and second ends 52, 54. The second diameter portion 48 has a side opening 56 that is in communication with the central passage 50 such that the internal storage space, central passage 50 and side opening 56 together form a continuum when the sampling bottle is placed in the receptacle 42.

The elongated tube 16 has a bore and first and second ends. The second end of the tube 16 has a flange 18 that is dimensioned and configured to abuttingly contact the first end 52 of the second diameter portion 48 of the coupling adapter 44 when the second end 54 of the tube 16 is inserted into the central passage 50 of the coupling adapter 44. A coupling nut 70 having a central opening with a diameter that is smaller than the tube 16 joins the tube 16 and the receptacle 42. The coupling nut 70 threadably engages the receptacle 42 such that the flange 18 is firmly gripped between the first end 52 of the second diameter portion 48 of the coupling adapter 44 and the coupling nut 70.

The elongated rod 26 has a first end and a second end and is dimensioned and configured to move axially within the bore of the tube 16. The first end of the rod 26 has a cylindrical bar attached at a right angle to the first end of the rod 26 such that a T-shaped handle 28 is formed. The second end of the rod 26 has a polytetrafluoroethylene (PTFE) plug 78 for sealing the side opening 56 of the coupling adapter 44. When the rod 26 is manipulated axially within the tube 16, the movement of the PTFE plug 78 results in the side opening 56 of the coupling adapter 44 being unblocked and allows a liquid sample to enter the bottle.

In use, the receptacle 42 is placed in the body of liquid from which the liquid sample is to be taken. By manipulating the elongated rod 26 axially within the tube 16, the PTFE plug 78 moves, which results in the side opening 56 of the coupling adapter 44 being unblocked. This allows a liquid sample to enter the bottle. Once the bottle is full, the rod 26 is manipulated again such that the PTFE plug 78 blocks the side opening 56 of the coupling adapter 44. The alternative liquid sampler 40 provides the advantage of using sterile bottles to collect the liquid samples, which will assure the validity of the sample drawn. Also, the alternative liquid sampler 40 provides the taking of unit dose samples, as small as 5.0 cc, from a user-determined location. The rod 26 has a protuberance 32 located near the first end. The tube 16 has a locking sleeve 64 near the first end. The locking sleeve 64 has a guiding slot 66 for receiving the protuberance 32 and a locking slot 68 for preventing the rod 26 from escaping from the tube 16 during sampling of the liquid.

It should also be noted that, although in the embodiment discussed here only one tube 16 and one rod 26 is discussed, any number of these can be arranged in an end-to-end arrangement with one another, leading to a alternative liquid sampler 40 of user determined length. All that is required is to have a tube 16 with a corresponding length. It should also be noted that although a T-shaped handle 28 is shown as the manipulating member, any number of appropriate shapes such as a ring or other shape could be used in the T-shaped handles 28 place to facilitate the manipulation of the device. In addition, the there is understood to have bottles that are threadably engageable directly with the coupling adapter 44 rather than placing the bottle into the receptacle 42.

Referring to FIG. 5, another embodiment of the liquid sampler 79 is shown. The liquid sampler 79 has multiple receptacles 12 to provide simultaneous sampling of a liquid from user determined locations. As in the preferred embodiment, the liquid sampler 79 allows the use of standard syringes in the sampling of the liquid. The liquid sampler 79 has at least two receptacles 12, each having a cylindrical sidewall, a bottom, an internal cavity for housing a syringe, a central opening 14 in the bottom, and a cap 84.

The central opening 14 allows the inlet opening of a syringe to communicate with the space external to the receptacle 12. The cap 84 has a central plunger opening 86 that acts as a closure for the receptacle 12. The central plunger opening 86 allows a portion of the plunger and finger pressure platform of a syringe that is housed in the receptacle 12 to protrude from the cap 84. The liquid sampler 79 has an elongated tube 88 having a bore, first and second ends with each of the receptacles 12 being fixed to the tube 88 at predetermined locations.

An elongated rod 26 is dimensioned and configured to move axially within the bore of the tube 88. The rod 26 has first and second ends with the first end having a cylindrical bar attached at a right angle to the first end such that a T-shaped handle 28 is formed. A plunger manipulating rod 106 is attached to the rod 26 near the rod's 26 handle 28, whereby the plunger manipulating rod 106 moves with the rod 26. Plunger connecting means 108 connect each plunger housed in a receptacle 12 to the plunger manipulating rod 106.

The rod 26 has a protuberance 32 located near the first end. The tube 88 has a volume scale sleeve 20 near the first end. Turning to FIG. 3 for more specific details of the volume scale sleeve 20, there is a guiding slot 22 in the volume scale sleeve 20 for receiving the protuberance 32. The volume scale sleeve 20 has indicia that are next to the guiding slot 22 that allow the user to determine the volume of the liquid sample in the syringe by inspection. If the user desires a specific volume be drawn, the volume scale sleeve 20 also has a plurality of locking slots 24 corresponding in their positions to a respective value for the volume of the sample of the liquid in the syringe. The locking slots 24 allow the user to lock the protuberance 32 in a specific locking slot 24 and fix the volume of the liquid sample to be drawn into the syringes.

In use, the receptacles 12 are placed in the body of liquid from which the liquid samples are to be taken and syringes are placed in each of the receptacles 12. By manipulating the elongated rod 26 axially within the tube 88, the plungers move substantially simultaneously within their respective syringe barrels to thereby fill each syringe with a sample of the liquid. Since the indicia on the volume scale sleeve 20 corresponds to the volume indicia on the syringe, the user can determine the volume of the liquid sample drawn by inspecting the location of the protuberance 32 relative to the volume scale sleeve 20. The liquid sampler 79 provides the advantage of using sterile disposable syringes to collect the liquid samples, which will assure the validity of the sample drawn. Also, the liquid sampler 79 provides the taking of unit dose samples, as small as 0.1 cc, from a user determined location.

It should also be noted that, although in the embodiment discussed here only one tube 88 and one rod 26 is discussed, any number of these can be arranged in an end-to-end arrangement with one another, leading to a liquid sampler of user-determined length. All that is required is to have a tube 88 with a corresponding length. It should also be noted that although a T-shaped handle 28 is shown as the manipulating member, any number of appropriate shapes such as a ring or other shape could be used in the T-shaped handles 28 place to facilitate the manipulation of the device.

It is to be understood that the present invention is not limited to the embodiments described above, but encompasses any and all embodiments within the scope of the following claims.

I claim:

1. A liquid sampling device for obtaining samples of a liquid from user determined locations within a body of the liquid, said liquid sampling device allowing the use of a standard syringe in the sampling of the liquid, the standard syringe having a barrel, an inlet opening communicating with the syringe barrel and a plunger slidably supported within the barrel, the plunger having a finger pressure platform, said liquid sampling device comprising:

a receptacle having a top opening, an internal cavity, a cylindrical sidewall and a bottom, said bottom having a central opening, said internal cavity being dimensioned and configured to house the syringe barrel, said central opening allowing the inlet opening of the syringe barrel to communicate with space external to said receptacle;

an elongated hollow tube having a bore, a first end, and a second end, said second end of said tube having a flange dimensioned and configured to abuttingly contact said top opening of said receptacle;

an elongated rod having a first end and a second end, said first end of said elongated rod having a handle means, said second end of said elongated rod having an attaching means for releasably attaching the plunger of the syringe to said second end of said elongated rod, said elongated rod being dimensioned to move axially within said bore of said tube; and a coupling nut having a central opening smaller in diameter than said flange of said tube and being threadably engageable with said receptacle, such that when said coupling nut is threadedly engaged with said receptacle said flange is firmly gripped between said coupling nut and said receptacle;

whereby with the receptacle positioned proximate a user-determined location within the body of the liquid, manipulating said elongated rod allows the moving of the plunger within the syringe barrel to thereby fill the syringe barrel with a sample of the liquid.

2. The liquid sampling device according to claim 1, further comprising a volume scale sleeve provided at said first end of said tube, said rod having a protuberance projecting outwardly proximate to said first end of said rod, said volume scale sleeve having a guiding slot for receiving said protuberance, and said volume scale sleeve having indicia provided adjacent said slot, whereby said indicia allow determination of the volume of the sample of the liquid within the syringe by visual inspection.

3. The liquid sampling device according to claim 2, wherein said volume scale sleeve has a plurality of locking slots extending perpendicularly from said guiding slot, each of said plurality of locking slots corresponding in position to a respective value for the volume of the sample of the liquid in the syringe, whereby said rod can be locked in position by rotating said protuberance into engagement with a selected one of said plurality of locking slots thereby to fix the volume of the sample of the liquid within the syringe at the volume corresponding to said selected one of said plurality of locking slots.

4. The liquid sampling device according to claim 1, wherein said attaching means for releasably attaching the plunger of the syringe includes a T-shaped groove dimensioned and configured to receive the finger pressure platform of the plunger therein.

5. The liquid sampling device according to claim 1, wherein said handle means includes a cylindrical bar attached at a right angle to said first end of said elongated rod so as to form a T-shaped handle.

* * * * *